(12) United States Patent
Ribble et al.

(10) Patent No.: US 9,761,109 B2
(45) Date of Patent: *Sep. 12, 2017

(54) OCCUPANT EGRESS PREDICTION SYSTEMS, METHODS AND DEVICES

(71) Applicant: Hill-Rom Services, Inc., Batesville, IN (US)

(72) Inventors: David L. Ribble, Indianapolis, IN (US); Michelle E. McCleerey, Raleigh, NC (US); Eric D. Agdeppa, Cincinnati, OH (US); Michael S. Hood, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/383,462

(22) Filed: Dec. 19, 2016

(65) Prior Publication Data

US 2017/0098360 A1 Apr. 6, 2017

Related U.S. Application Data

(63) Continuation of application No. 14/857,006, filed on Sep. 17, 2015, now Pat. No. 9,552,714, which is a (Continued)

(51) Int. Cl.
*G08B 21/02* (2006.01)
*G08B 21/04* (2006.01)
(Continued)

(52) U.S. Cl.
CPC ........ *G08B 21/0461* (2013.01); *A61B 5/1115* (2013.01); *A61B 5/6892* (2013.01);
(Continued)

(58) Field of Classification Search
None
See application file for complete search history.

(56) References Cited

U.S. PATENT DOCUMENTS 2,194,809 A 3/1940 Powell, Jr.
3,325,799 A 6/1967 Farris
(Continued)

FOREIGN PATENT DOCUMENTS

EP 2417908 2/2012
JP 06315424 A2 11/1994
(Continued)

OTHER PUBLICATIONS

Sufi et al., "A mobile phone based intelligent scoring approach for assessment of critical illness", *Technology and Applications in Biomedicine*, 2008. ITAB 2008. International Conference on, IEEE, Piscataway, NJU, USA, May 30, 2008, pp. 290-293, XP031289425.
(Continued)

*Primary Examiner* — Brent Swarthout
(74) *Attorney, Agent, or Firm* — Barnes & Thornburg LLP

(57) ABSTRACT

A method comprises determining a person's level of risk for developing an adverse condition; selecting a care protocol based on the level of risk; displaying a proposed configuration of a person support structure corresponding to the care protocol for a caregiver to approve; and upon approval by the caregiver, implementing the configuration.

16 Claims, 11 Drawing Sheets

Related U.S. Application Data continuation of application No. 13/900,115, filed on May 22, 2013, now Pat. No. 9,165,449.

(60) Provisional application No. 61/650,046, filed on May 22, 2012.

(51) Int. Cl.
  *A61B 5/11* (2006.01)
  *A61B 5/00* (2006.01)
  *A61G 7/012* (2006.01)
  *A61G 7/015* (2006.01)
  *A61G 7/05* (2006.01)
  *A61G 7/057* (2006.01)

(52) U.S. Cl.
  CPC .............. *A61B 5/746* (2013.01); *A61G 7/012* (2013.01); *A61G 7/015* (2013.01); *A61G 7/051* (2016.11); *A61G 7/05769* (2013.01); *G08B 21/0423* (2013.01); *A61G 2203/34* (2013.01)

(56) References Cited

U.S. PATENT DOCUMENTS

| | | |
|---|---|---|
| 3,631,438 A | 12/1971 | Lewin |
| 3,644,950 A | 2/1972 | Lindsay, Jr. |
| 3,727,606 A | 4/1973 | Sielaff |
| 3,836,900 A | 9/1974 | Mansfield |
| 3,996,928 A | 12/1976 | Marx |
| 4,146,885 A | 3/1979 | Lawson, Jr. |
| 4,195,287 A | 3/1980 | McCoy et al. |
| 4,245,651 A | 1/1981 | Frost |
| 4,422,458 A | 12/1983 | Kravath |
| 4,481,686 A | 11/1984 | Lacoste |
| 4,483,029 A | 11/1984 | Paul |
| 4,485,505 A | 12/1984 | Paul |
| 4,525,885 A | 7/1985 | Hunt et al. |
| 4,554,930 A | 11/1985 | Kress |
| 4,559,656 A | 12/1985 | Foster |
| 4,564,965 A | 1/1986 | Goodwin |
| 4,595,023 A | 6/1986 | Bonnet |
| 4,602,643 A | 7/1986 | Dietz |
| 4,637,083 A | 1/1987 | Goodwin |
| 4,657,026 A | 4/1987 | Tagg |
| 4,677,857 A | 7/1987 | Feldmann |
| 4,681,098 A | 7/1987 | Lee |
| 4,694,520 A | 9/1987 | Paul et al. |
| 4,757,825 A | 7/1988 | Diamond |
| 4,799,276 A | 1/1989 | Kadish |
| 4,838,309 A | 6/1989 | Goodwin |
| 4,889,131 A | 12/1989 | Salem et al. |
| 4,934,468 A | 6/1990 | Koerber, Sr. et al. |
| 4,935,968 A | 6/1990 | Hunt et al. |
| 4,942,635 A | 7/1990 | Hargest et al. |
| 4,949,412 A | 8/1990 | Goode |
| 4,949,414 A | 8/1990 | Thomas et al. |
| 4,967,195 A | 10/1990 | Shipley |
| 4,971,065 A | 11/1990 | Pearce |
| 5,010,772 A | 4/1991 | Bourland et al. |
| 5,052,067 A | 10/1991 | Thomas et al. |
| 5,057,819 A | 10/1991 | Valenti |
| 5,060,174 A | 10/1991 | Gross |
| 5,101,828 A | 4/1992 | Welkowitz et al. |
| 5,117,518 A | 6/1992 | Schlid |
| 5,170,364 A | 12/1992 | Gross et al. |
| 5,182,826 A | 2/1993 | Thomas et al. |
| 5,184,112 A | 2/1993 | Gusakov |
| 5,276,432 A | 1/1994 | Travis |
| 5,283,735 A | 2/1994 | Gross et al. |
| 5,539,942 A | 7/1996 | Melou |
| 5,561,412 A | 10/1996 | Novak et al. |
| 5,664,270 A | 9/1997 | Bell et al. |
| 5,738,102 A | 4/1998 | Lemelson |
| 5,794,288 A | 8/1998 | Soltani et al. |
| 5,815,864 A | 10/1998 | Sloop |
| 5,817,146 A | 10/1998 | Augustine |
| 5,829,081 A | 11/1998 | Pearce |
| 5,873,137 A | 2/1999 | Yavets-Chen |
| 5,934,280 A | 8/1999 | Viard et al. |
| 5,964,720 A | 10/1999 | Pelz |
| 5,970,789 A | 10/1999 | Meyer et al. |
| 6,009,580 A | 1/2000 | Caminade et al. |
| 6,011,477 A | 1/2000 | Teodorescu et al. |
| 6,034,526 A | 3/2000 | Montant et al. |
| 6,067,019 A | 5/2000 | Scott |
| 6,067,466 A | 5/2000 | Selker et al. |
| 6,079,068 A | 6/2000 | Viard |
| 6,094,762 A | 8/2000 | Viard et al. |
| 6,208,250 B1 | 3/2001 | Dixon et al. |
| 6,212,718 B1 | 4/2001 | Stolpmann et al. |
| 6,493,568 B1 | 12/2002 | Bell et al. |
| 6,560,804 B2 | 5/2003 | Wise et al. |
| 6,721,980 B1 | 4/2004 | Price et al. |
| 6,739,006 B2 | 5/2004 | Borders et al. |
| 6,984,207 B1 | 1/2006 | Sullivan et al. |
| 7,031,857 B2 | 4/2006 | Tarassenko et al. |
| 7,077,810 B2 | 7/2006 | Lange et al. |
| 7,127,948 B2 | 10/2006 | Tavares et al. |
| 7,183,930 B2 | 2/2007 | Basir et al. |
| 7,242,306 B2 | 7/2007 | Wildman et al. |
| 7,242,308 B2 | 7/2007 | Ulrich et al. |
| 7,245,956 B2 | 7/2007 | Matthews et al. |
| 7,248,933 B2 | 7/2007 | Wildman |
| 7,253,366 B2 | 8/2007 | Bhai |
| 7,289,844 B2 | 10/2007 | Misczynski et al. |
| 7,296,312 B2 | 11/2007 | Menkedick et al. |
| 7,304,580 B2 | 12/2007 | Sullivan et al. |
| 7,306,564 B2 | 12/2007 | Nakatani et al. |
| 7,314,451 B2 | 1/2008 | Halperin et al. |
| 7,315,535 B2 | 1/2008 | Schuman |
| 7,319,386 B2 | 1/2008 | Collins, Jr. et al. |
| 7,330,127 B2 | 2/2008 | Price et al. |
| 7,443,303 B2 | 10/2008 | Spear et al. |
| 7,472,956 B2 | 1/2009 | Makhsous et al. |
| 7,515,059 B2 | 4/2009 | Price et al. |
| 7,629,890 B2 | 12/2009 | Sullivan et al. |
| 7,973,666 B2 | 7/2011 | Petrosenko et al. |
| 9,165,449 B2 * | 10/2015 | Ribble ............ A61B 5/746 |
| 9,552,714 B2 * | 1/2017 | Ribble ............ A61B 5/746 |
| 2001/0004778 A1 | 6/2001 | Heimbrock et al. |
| 2003/0144829 A1 | 7/2003 | Geatz et al. |
| 2004/0111045 A1 | 6/2004 | Sullivan et al. |
| 2004/0149711 A1 | 8/2004 | Wyatt et al. |
| 2005/0027416 A1 | 2/2005 | Basir et al. |
| 2005/0124864 A1 | 6/2005 | Mack et al. |
| 2005/0165284 A1 | 7/2005 | Gefen |
| 2005/0168341 A1 | 8/2005 | Reeder et al. |
| 2005/0190062 A1 | 9/2005 | Sullivan et al. |
| 2005/0190068 A1 | 9/2005 | Gentry et al. |
| 2005/0273940 A1 | 12/2005 | Petrosenko |
| 2006/0101581 A1 | 5/2006 | Blanchard et al. |
| 2006/0169282 A1 | 8/2006 | Izumi et al. |
| 2006/0179952 A1 | 8/2006 | Tavares et al. |
| 2007/0118054 A1 | 5/2007 | Pinhas et al. |
| 2007/0210917 A1 | 9/2007 | Collins, Jr. et al. |
| 2007/0247316 A1 | 10/2007 | Wildman et al. |
| 2008/0015903 A1 | 1/2008 | Rodgers |
| 2008/0060138 A1 | 3/2008 | Price et al. |
| 2008/0094207 A1 | 4/2008 | Collins, Jr. et al. |
| 2008/0095156 A1 | 4/2008 | Schuman |
| 2008/0096307 A1 | 4/2008 | Basol |
| 2008/0114260 A1 | 5/2008 | Lange et al. |
| 2008/0146892 A1 | 6/2008 | LeBoeuf et al. |
| 2008/0169931 A1 * | 7/2008 | Gentry .................. A61B 5/1113 340/573.1 |
| 2008/0269625 A1 | 10/2008 | Halperin et al. |
| 2008/0275349 A1 | 11/2008 | Halperin et al. |
| 2008/0281170 A1 | 11/2008 | Eshelman et al. |
| 2009/0054735 A1 | 2/2009 | Higgins et al. |
| 2009/0062623 A1 | 3/2009 | Cohen |
| 2009/0069642 A1 | 3/2009 | Gao et al. |
| 2009/0088606 A1 | 4/2009 | Chuddihy et al. |
| 2009/0093686 A1 | 4/2009 | Hu et al. |

(56) References Cited

U.S. PATENT DOCUMENTS

| | | |
|---|---|---|
| 2009/0095877 A1 | 4/2009 | Poo |
| 2009/0163774 A1 | 6/2009 | Thatha et al. |
| 2009/0216556 A1 | 8/2009 | Martin et al. |
| 2009/0326339 A1 | 12/2009 | Horvitz |
| 2010/0099954 A1 | 4/2010 | Dickinson et al. |
| 2010/0170043 A1 | 7/2010 | Young et al. |
| 2010/0174198 A1 | 7/2010 | Young et al. |
| 2011/0010014 A1 | 1/2011 | Oexman et al. |
| 2011/0068935 A1 | 3/2011 | Riley et al. |
| 2011/0071851 A1* | 3/2011 | Alden .................. G06F 19/327 705/3 |
| 2011/0163885 A1 | 7/2011 | Poulos et al. |
| 2011/0302719 A1 | 12/2011 | Schwirian et al. |
| 2012/0075464 A1* | 3/2012 | Derenne .............. A61B 5/0013 348/135 |
| 2012/0089419 A1 | 4/2012 | Huster et al. |
| 2012/0174322 A1 | 7/2012 | Skinner et al. |
| 2012/0253142 A1* | 10/2012 | Meger .................. A61B 5/1116 600/301 |
| 2013/0205501 A1* | 8/2013 | Robertson ............. A61G 7/018 5/611 |
| 2014/0000032 A1* | 1/2014 | Dixon .................. A61G 7/0528 5/611 |
| 2014/0046209 A1* | 2/2014 | Klap .................... A61B 5/0205 600/534 |
| 2014/0137025 A1 | 5/2014 | Newkirk et al. |
| 2016/0005289 A1 | 1/2016 | Ribble et al. |

FOREIGN PATENT DOCUMENTS

| | | |
|---|---|---|
| WO | 2008/096307 | 8/2008 |
| WO | 2009/095877 | 8/2009 |

OTHER PUBLICATIONS

European search report from EP 10 17 6765, dated Feb. 16, 2011 (11 pages).

European search report for EP Application 13168769; Place of Search—the Hague; date of completion of the search—Oct. 30, 2013.

L. Tarassenko et al, "Biosign™; Multi-Parameter Monitoring for Early Warning of Patient Deterioration" (6 pages).

C. P. Subbe et al., "Validation of a modified Early Warning Score in medical admissions", *Q J Med* 2001; 94:521-526.

Marilyn Hravnak et al., "Defining the Incidence of Cardiorespiratory Instability in Patients in Step-down Units Using an Electronic Integrated Monitoring System", *Arch Intern Med*, vol. 168 (No. 12), Jun. 23, 2008, 1300-1308.

L. Tarassenko et al., "Integrated monitoring and analysis for early warning of patient deterioration", *British Journal of Anasthesia*, May 17, 2006 (5 pages).

"Visensia", *OBS Medical Ltd*. (4 pages).

Coba V. Rubinfeld I, et al., "Can the Visensia Index Score Predict Mortality in High Risk Injured Patients?" (1 page).

* cited by examiner

OCCUPANT EGRESS PREDICTION SYSTEMS, METHODS AND DEVICES

This application is a continuation of U.S. application Ser. No. 14/857,006, filed Sep. 17, 2015, now U.S. Pat. No. 9,552,714, which is a continuation of U.S. application Ser. No. 13/900,115, filed May 22, 2013, now U.S. Pat. No. 9,165,449, which claims the benefit of U.S. Provisional Application No. 61/650,046, filed May 22, 2012, and each of which are hereby incorporated herein by reference.

BACKGROUND OF THE DISCLOSURE

This disclosure relates generally to occupant egress prediction systems, devices and methods. More particularly, but not exclusively, one contemplated embodiment relates to a system configured to determine when an occupant supported on a person support structure is going to egress from the person support structure. While various systems have been developed, there is still room for improvement. Thus, a need persists for further contributions in this area of technology.

SUMMARY OF THE DISCLOSURE

A method comprises sensing a first characteristic indicative of an occupant's status on an occupant support structure; sensing a second characteristic indicative of an occupant's status on the occupant support structure; comparing the first characteristic to the second characteristic; if the difference between the first characteristic and the second characteristic is greater than a predetermined threshold, alerting a caregiver that the occupant is preparing to exit the occupant support structure.

A system comprises an occupant support structure, a sensor, and a control system. The occupant support structure is configured to support an occupant thereon. The sensor is coupled to the occupant support structure and configured to sense a characteristic of the occupant supported on the occupant support structure. The control system is configured to determine when the occupant is preparing to exit the occupant support structure as a function of the characteristic sensed by the sensor.

A method comprises receiving information corresponding to at least one of the position, orientation, and activity level of a person supported on a person support apparatus, comparing the characteristic to a predetermined threshold; if the characteristic exceeds the predetermined threshold, alerting a caregiver that the person will likely attempt to egress from the person support structure in the near future.

A method comprises receiving at least one characteristic of at least one of a person support structure, a person supported on the person support structure, and a facility where the person and the person support structure are located; assigning a value to each of the at least one characteristic; summing the values for the at one characteristic; comparing the summed values to a predetermined threshold; if the summed values exceed the predetermined threshold, alerting a caregiver that the person will likely attempt to egress from the person support structure in the near future.

Additional features alone or in combination with any other feature(s), including those listed above and those listed in the claims and those described in detail below, can comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

Referring now to the illustrative examples in the drawings, wherein like numerals represent the same or similar elements throughout.

DETAILED DESCRIPTION OF THE DRAWINGS

Figure 1:
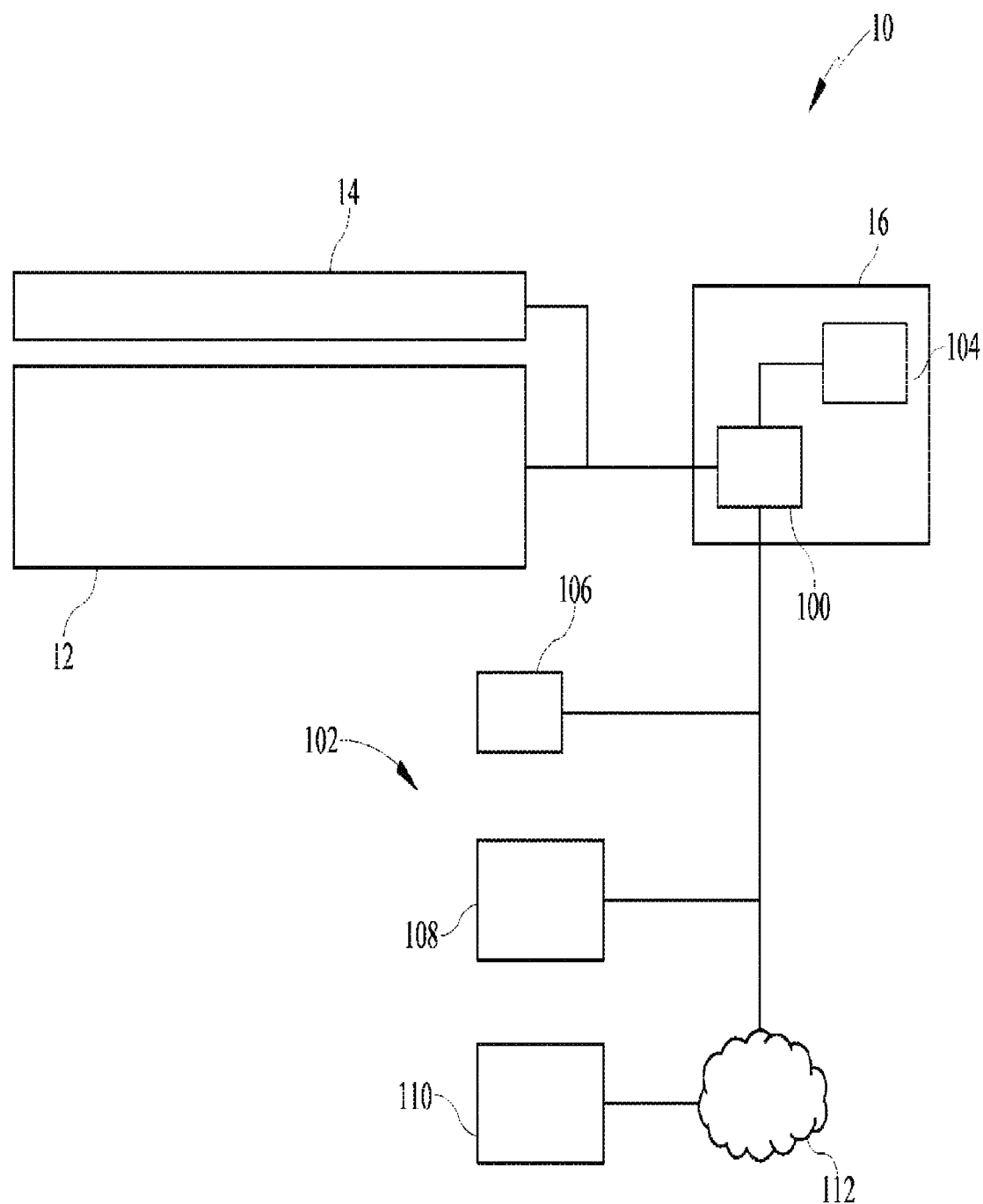
FIG. 1 is a diagrammatic view of the occupant egress prediction system including a person support apparatus, a mattress, and a control system according to one contemplated embodiment of the disclosure.

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

FIG. 1 shows an occupant egress prediction system 10 according to one contemplated embodiment. The occupant egress prediction system 10 includes a person support apparatus 12, a person support surface 14 or mattress 14, and a control system 16. In some contemplated embodiments, the person support apparatus 12 is a hospital bed frame and the mattress 14 is supported thereon. In other contemplated embodiments, the person support apparatus 12 can be a stretcher, an operating room table, or other person supporting structure. The person support apparatus 12 includes a lower frame 17, supports 18 or lift mechanisms 18 coupled to the lower frame 17, and an upper frame 20 movably supported above the lower frame 17 by the supports 18. The lift mechanisms 18 are configured to raise and lower the upper frame 20 with respect to the lower frame 17 and move the upper frame 20 between various orientations, such as, Trendelenburg and reverse Trendelenburg.

Figure 2:
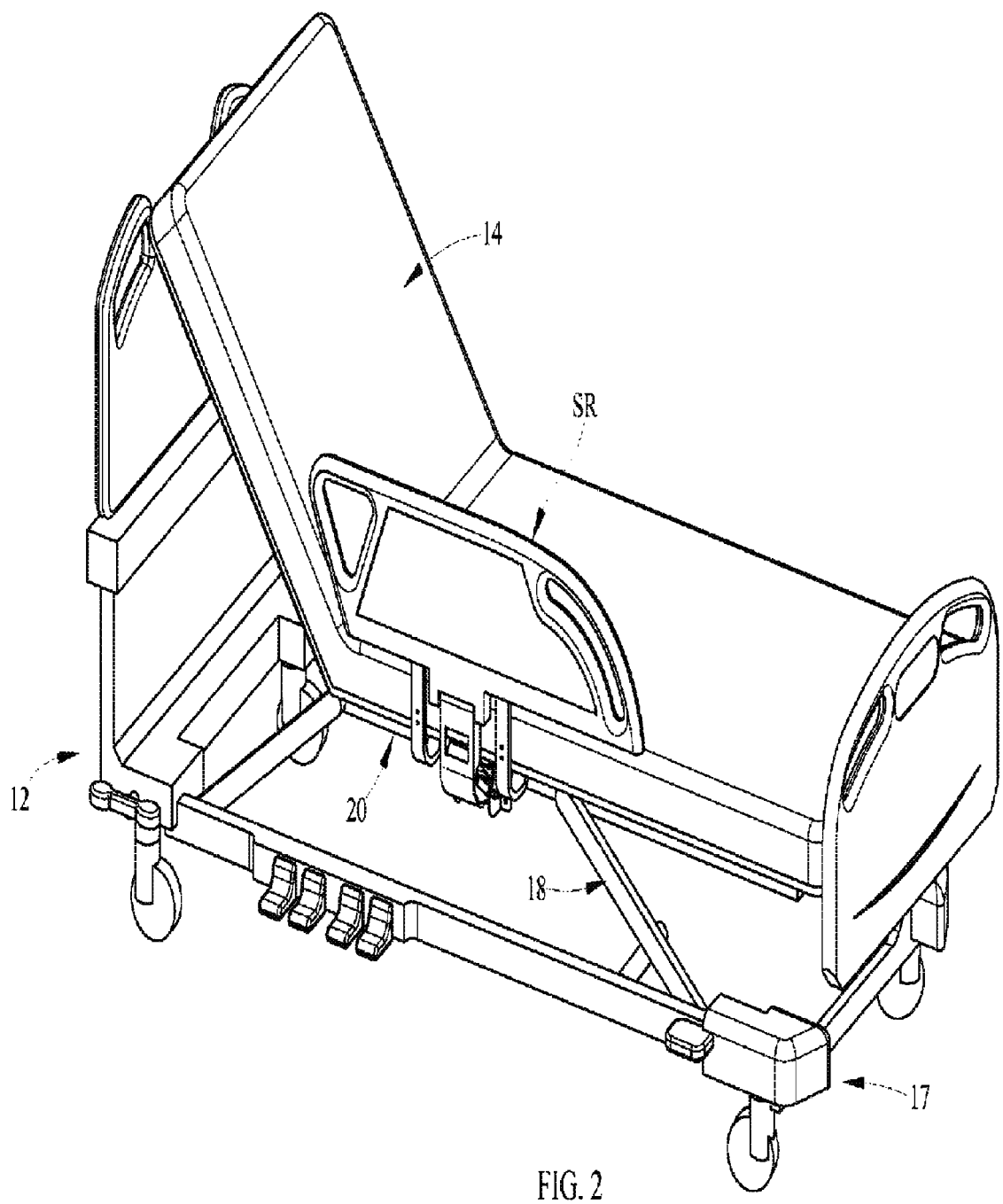
FIG. 2 is a side perspective view of the person support apparatus of FIG. 1.
Figure 3:
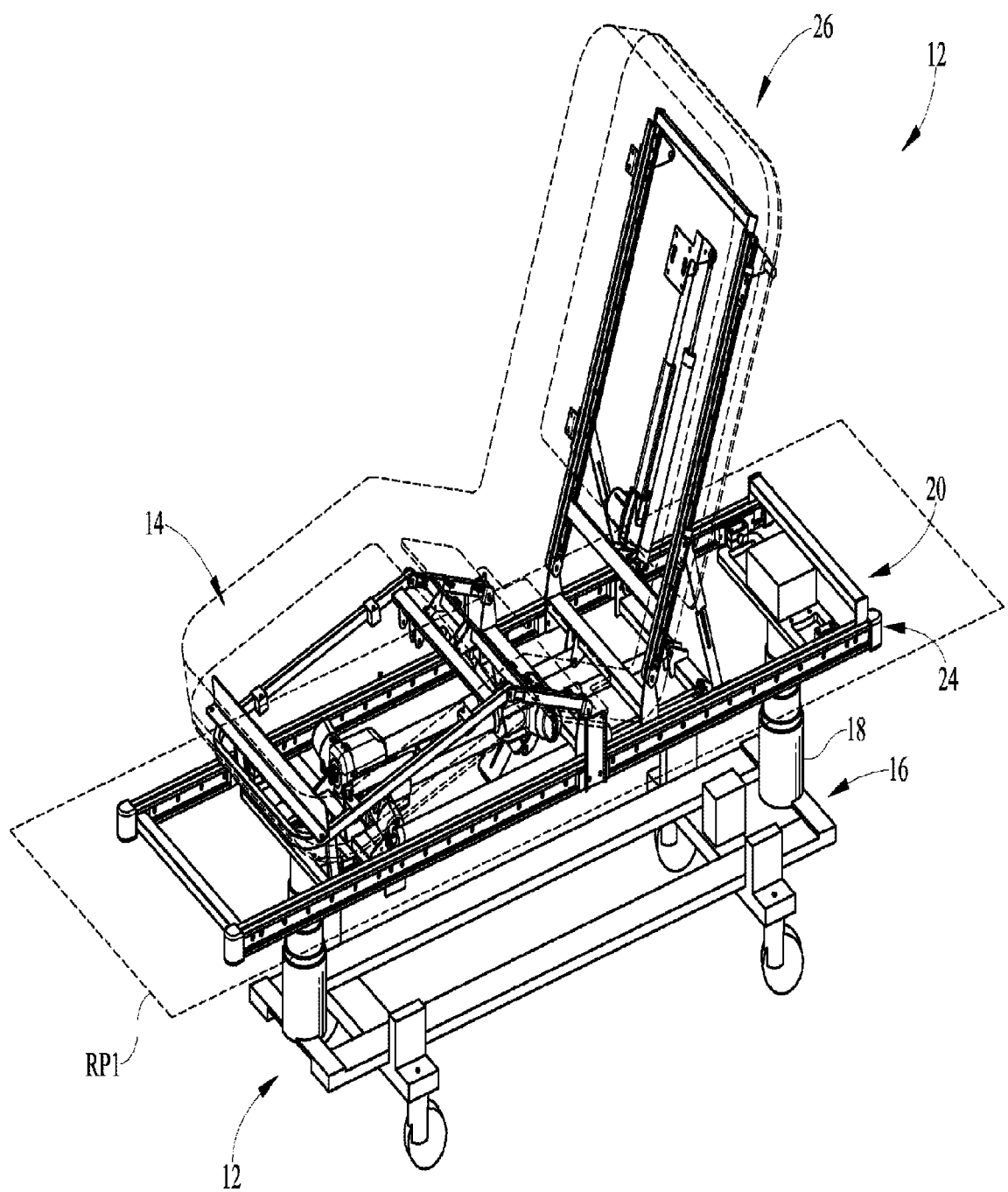
FIG. 3 is a side perspective view of the person support apparatus of FIG. 1 showing the various components of the upper and lower frame.
Figure 4:
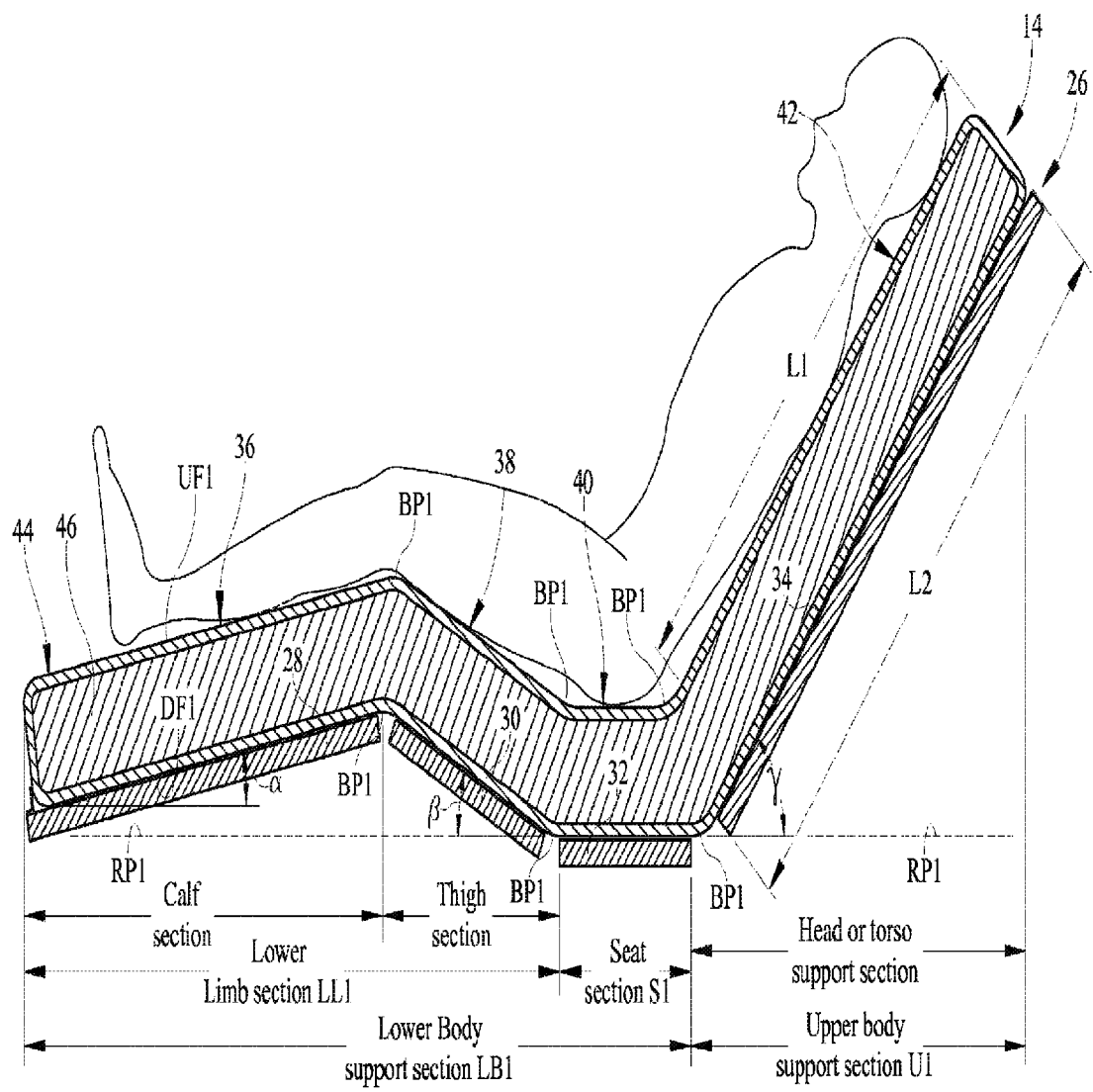
FIG. 4 is a side cross-sectional view of the mattress of FIG. 1 showing the various sections and how they correspond to the sections of the upper frame that support the mattress.

The upper frame 20 includes an upper frame base 24, a deck 26 coupled to the upper frame base 24, and a plurality of siderails SR as shown in FIGS. 2-4. The deck 26 includes a calf section 28, a thigh section 30, a seat section 32, and a head and torso section 34 as shown in FIG. 3. The calf section 28 and the thigh section 30 define a lower limb support section LL1. The head and torso section 34 define an upper body support section U1. The seat section 32 defines the seat section S1. The calf section 28, the thigh section 30, and the seat section 32 define a lower body support section LB1. At least the calf section 28, the thigh section 30, and the head and torso section 34 are movable with respect to one another and/or the upper frame base 24. In some contemplated embodiments, the calf section 28, the thigh section 30, the seat section 32, and the head and torso section 34 cooperate to move the person support apparatus 12 between an substantially planar or lying down configuration and a chair configuration. In some contemplated embodiments, the calf section 28, the thigh section 30, the seat section 32, and the head and torso section 34 cooperate to move the person support apparatus 12 between a substantially planar or lying down configuration and an angled or reclined configuration. In some contemplated embodiments, the head and torso section 34 is moved such that it is at an angle of at least about 30° with respect to a reference plane RP1 passing through the upper frame 20.

Figure 5:
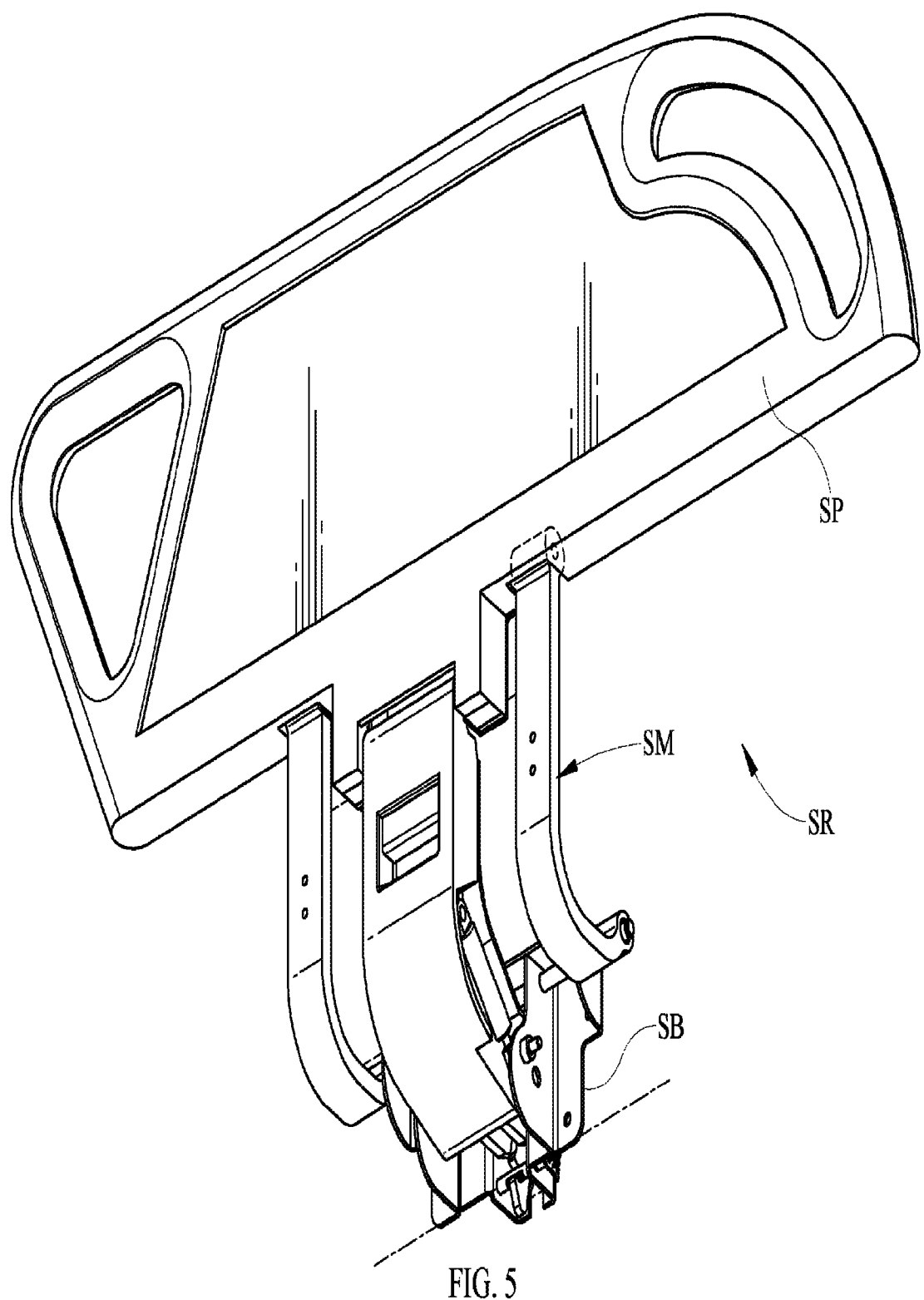
FIG. 5 is a side perspective view of the siderail coupled to the person support apparatus of FIG. 1 showing the base, the movement mechanism and the panel.

The siderails SR are configured to move between a deployed position and a storage position, and are used to locate the perimeter of the upper frame 24 and assist with ingress/egress to/from the person support apparatus 12. The siderails include a base SB, a movement mechanism SM movably coupled to the base SB, and a panel SP movably coupled to the movement mechanism SM as shown in FIG. 5. In some contemplated embodiments, a sensor (not shown) is coupled to the siderail SR and configured to sense whether the siderail SR is in the deployed position or in the storage position. In some contemplated embodiments, the sensor is a switch coupled to the movement mechanism SM and which is configured to close when the siderail SR reaches the deployed position and open when the siderail SR moves from the deployed position toward the storage position. In some contemplated embodiments, the sensor can be a contact sensor coupled to the latch mechanism (not shown) that can indicate when the latch mechanism is configured to maintain the siderail SR in the deployed position, or a sensor configured to sense light from a light source that is reflected off the movement mechanism SM when the siderail SR is in the deployed position.

Figure 6:
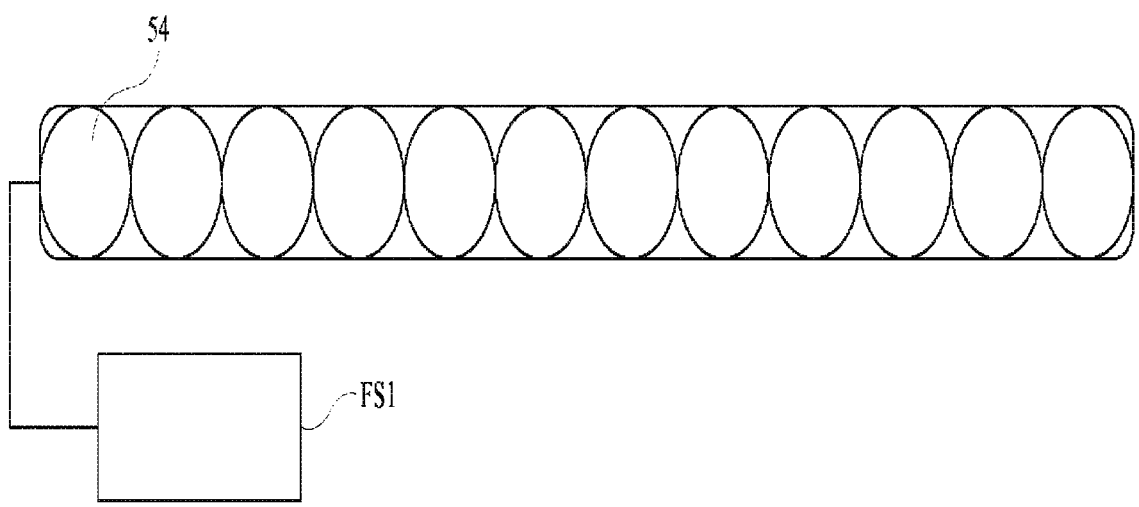
FIG. 6 is a partial diagrammatic view of the mattress of FIG. 1 showing the bladders and fluid supply.

The person support surface 14 is configured to support a person thereon and move with the deck 20 between the various configurations. In some contemplated embodiments, the person support surface 14 is a hospital bed mattress 14 as shown in FIGS. 4 and 6. In some contemplated embodiments, the person support surface 14 is a consumer mattress. In some contemplated embodiments, the person support surface 14 includes a heat and moisture regulating topper positioned on the mattress. In some contemplated embodiments, the person support surface can include a pressure mapping mat positioned on the mattress. The person support surface 14 includes a calf portion 36, a thigh portion 38, a seat portion 40, and a head and torso portion 42 as shown in FIG. 3, which is supported on corresponding sections of the deck 26. In one contemplated embodiment, the deck sections help move and/or maintain the various portions of the mattress 14 at angles $\alpha$, $\beta$ and $\gamma$ with respect to the reference plane RP1. In some contemplated embodiments, the person support surface 14 is a non-powered (static) surface. In some contemplated embodiments, the person support surface 14 is a powered (dynamic) surface configured to receive fluid from a fluid supply FS1 as shown in FIG. 6.

The person support surface 14 includes a mattress cover 44 and a mattress core 46 enclosed by the mattress cover 44. The mattress core 46 can be composed of a single type of material or a combination of materials and/or devices. In the case of a powered surface, the mattress core 46 includes at least one fluid bladder 54 therein that receives fluid from a fluid supply (not shown) to maintain the fluid pressure within the fluid bladder 54 at a predetermined level. In some contemplated embodiments, the powered surface can include non-powered components, such as, a foam frame that at least one fluid bladder 54 is positioned between. In some contemplated embodiments, wedge shaped bladders are mirrored laterally about the centerline of the mattress 14 and are configured to be inflated consecutively to laterally tilt the occupant, thereby relieving pressure on various portions of the occupant's body to help reduce the occurrences of pressure ulcers.

In the case of a non-powered surface, the mattress core 46 is composed of a cellular engineered material, such as, single density foam. In some contemplated embodiments, the mattress core 46 includes at least one bladder 54, such as, a static air bladder or a static air bladder with foam contained there within, a metal spring and/or other non-powered support elements or combinations thereof. In some contemplated embodiments, the mattress core 46 and includes multiple zones with different support characteristics configured to enhance pressure redistribution as a function of the proportional differences of a person's body. Also, in some embodiments, the mattress core 46 includes various layers and/or sections of foam having different impression load deflection (ILD) characteristics, such as, in the NP100 Prevention Surface, AccuMax Quantum™ VPC Therapy Surface, and NP200 Wound Surfaces sold by Hill-Rom®.

The control system 16 is configured to determine when an occupant is preparing to egress from the person support structure. The control system 16 includes a processor 100, an input 102, and memory 104. In some contemplated embodiments, the input 102 is a sensor 106, such as, an image capture device or video camera, a 3D image sensor, a pressure sensor, a temperature sensor, an acoustic sensor, a force sensor, a moisture sensor or other sensor configured to provide patient and environmental information to the processor 100 that is indicative of a physiological characteristic of the occupant, such as, the occupant's heart rate, respiration rate, respiration amplitude, skin temperature, weight, sleep state, body orientation, position and/or other information, a characteristic of the person support apparatus 12 or mattress, such as, whether the siderail SR is in the deployed or storage position, the status of a therapy, the height of the person support apparatus, the configuration of the person support apparatus 12 and/or mattress 14 or other information, and/or a relationship between the occupant and the person support apparatus 12 or mattress 14, such as, the person's position, orientation, activity and/or other information. In some contemplated embodiments, the sensors 106 are incorporated into the person support surface 14 or in a topper positioned on the person support surface 14, for example, as disclosed in U.S. Pat. No. 7,515,059 to Price et al. and U.S. Patent Publication No. 2011/0068928 to Riley et al. In some contemplated embodiments, the sensors 106 are load cells coupled to the upper frame 20. In some contemplated embodiments, the input 102 is a user interface 108 configured to receive information from a caregiver or other user. In other contemplated embodiments, the input 102 is an Electronic Medical Record (EMR) system 110 in communication with the processor 100 via a hospital network 112. In some contemplated embodiments, the processor 100 can output information, automatically or manually upon caregiver input, to the EMR for charting, which can include therapy initiation and termination, adverse event occurrence information, therapy protocol used, caregiver ID, and any other information associated with the occupant, caregiver, person support apparatus 12, person support surface 14, and adverse event. In some contemplated embodiments, the input 102 is a pressure mapping mat positioned on the person support surface 14.

The inputs 102 provide patient and environmental information that may include both spatial and temporal components and may relate to a variety of things, including, but not limited to, the person's current diagnosis, medications the person is taking, the person's physiological characteristics, the person's medical history, risk assessments performed by a caregiver, medical procedures the person has undergone, the status of medical equipment in the vicinity of the person or that is associated with the person (i.e., the person support apparatus 12 and the person support surface 14), care facility protocols and procedures, care facility logistics, caregiver or patient inputs, and other information about the person, medical devices, caregivers, and care facility that can be provided by an EMR or a patient activity log, gathered by and from the person support apparatus 12 and mattress 14 and other medical devices assigned to the person, or through the care facility network. The information from the inputs 102 can be grouped into the following categories: prerequisite condition inputs, motivating condition inputs, preparation sequence inputs, facility/unit inputs, and caregiver/patient inputs. Prerequisite condition inputs and motivating condition inputs can come from a number of sources, including, but not limited to, the occupant's electronic medical EMRs, patient activity logs, caregiver notes or activity logs, information sensed and tracked by the occupant support structure, the hospital network, or other sources of information. The prerequisite condition inputs include information that makes it more likely that an occupant could egress from the person support structure 12. One example of a prerequisite condition is whether the siderail coupled to the person support structure 12 is lowered so that a person can egress from the support structure. Another example of a prerequisite condition input is whether the person is conscious.

The motivating condition inputs include information that could make it more likely that a person would need or want to egress from the person support structure 12. One example of a motivating condition input includes objective factors that, if detected would indicate that the person needs to go to the bathroom and will attempt to egress from the support structure 12 in the near future, such as, the person being able to walk, increased movement of the person on the support structure 12, greater than 6 hours since the person last toileted, an I/O balance of greater than 400 mL, a lack of catheterization, and a lack of an incontinence pad, among others.

The preparation sequence inputs include information about the person's movement, posture, and other activities over time that are indicative of a person preparing to egress from the support structure. Preparation sequence inputs can be sensed using techniques that include, but are not limited to, image capture, pressure sensing, visual sensing, motion detection, position detection, and proximity detection, and are distinguishable from other inputs that do not generally indicate that a person is preparing to egress from the support structure 12. One example of a preparation sequence is where a person moves from an initial position, i.e., the supine position, to a position where the person is increasing the amount of weight supported by their pivoting elbow and/or increases their torso angle with respect to the support structure 12.

The patient/caregiver inputs include information entered by the caregiver and/or the patient. In some contemplated embodiments, the patient/caregiver inputs and facility/unit inputs can be used to adjust the weighting of the other inputs. One example of a patient/caregiver input is the caregiver's personal preference for alarms. The facility/unit inputs include information about the facility's and/or the unit's protocols, logistics, and other information. Some examples of facility/unit inputs include the patient population, case-mix, culture, varying patterns of the facility and/or unit, risk tolerance (low-level or high-level), time of day, staffing levels, when the caregivers are going to be making their rounds, and likelihood of an alarm being responded to within a predetermined amount of time, among other things.

The memory 104 stores one or more instruction sets configured to be executed by the processor 100 when the occupant egress prediction system 10 is armed. In some contemplated embodiments, the occupant egress prediction system 10 is armed manually by the caregiver or automatically based on information from the patient's EMR, the caregiver, and/or a protocol triggered by the risk profile of the patient. The instruction sets define procedures 114 that cause the processor 100 to implement one or more protocols that alert a caregiver via a communication system (not shown) when the system 10 predicts that the person supported on the person support apparatus 12 will egress from the person support apparatus 12 in the near future.

The communication system can be used to alert a caregiver proximate to the person support apparatus 14 (i.e., in the same room or in the hall way connected to the room) and a caregiver remote from the person support apparatus 14. In some contemplated embodiments, the communication system is a patient/nurse call system that can include patient stations capable of generating hospital calls and a remote master station which can prioritize and store the calls. One example of such a system is disclosed in U.S. Pat. No. 5,561,412 issued on Oct. 1, 1996 to Novak et al., which is incorporated by reference herein in its entirety. Another example of such a system is disclosed in U.S. Pat. No. 4,967,195 issued on May 8, 2006 to Shipley, which is incorporated by reference herein in its entirety. In another illustrative embodiment, the communication system can include a status board that displays the alert. The communication system can alert the caregiver by posting the alert to a status board, using a nurse call system, directly contacting the caregiver on their phone or pager, providing a local alert over the facility PA system, and opening a connection that allows the caregiver to speak directly to the patient. The communication can also escalate the vigilance monitoring of the patient.

In another contemplated embodiment, the communication system is a system for transmitting voice and data in packets over a network with any suitable number of intra-room networks that can couple a number of data devices to an audio station, where the audio station couples the respective intra-room network to a packet based network. One example of such a system is disclosed in U.S. Pat. No. 7,315,535 issued on Jan. 1, 2008 to Schuman, which is incorporated by reference herein in its entirety. Another example of such a system is disclosed in U.S. Patent Publication No. 2008/0095156 issued on Apr. 24, 2008 to Schuman, which is incorporated by reference herein in its entirety.

In yet another contemplated embodiment, the communication system is included a patient/nurse call system, a nurse call/locating badge, an electronic medical record (EMR) database, and one or more computers programmed with work-flow process software. One example of such a system is disclosed in U.S. Patent Publication No. 2008/0094207 published on Apr. 24, 2008 to Collins, Jr. et al., which is incorporated by reference herein in its entirety. Another example of such a system is disclosed in U.S. Patent Publication No. 2007/0210917 published on Sep. 13, 2007 to Collins, Jr. et al., which is incorporated by reference herein in its entirety. Yet another example of such a system is disclosed in U.S. Pat. No. 7,319,386 published on Jan. 15, 2008 to Collins, Jr. et al., which is incorporated by reference herein in its entirety. It should be appreciated that the work-flow process software can be the NaviCare® software available from Hill-Rom Company, Inc. It should also be appreciated that the work-flow process software can be the system disclosed in U.S. Pat. No. 7,443,303 issued on Oct. 28, 2008 to Spear et al., which is incorporated by reference herein in its entirety. It should further be appreciated that the badge can be of the type available as part of the ComLinx™ system from Hill-Rom Company, Inc. It should also be appreciated that the badge can also be of the type available from Vocera Communications, Inc.

In still another contemplated embodiment, the communication system is configured to organize, store, maintain and facilitate retrieval of bed status information, along with the various non-bed calls placed in a hospital wing or ward, and remotely identify and monitor the status and location of the person support apparatus, patients, and caregivers. One example of such a system is disclosed in U.S. Pat. No. 7,242,308 issued on Jul. 10, 2007 to Ulrich et al., which is incorporated by reference herein in its entirety. It should be appreciated that the remote status and location monitoring can be the system disclosed in U.S. Pat. No. 7,242,306 issued on Jul. 10, 2007 to Wildman et al., which is incorporated by reference herein in its entirety. It should also be appreciated that the remote status and location monitoring can be the system disclosed in U.S. Patent Publication No. 2007/0247316 published on Oct. 25, 2007 to Wildman et al., which is incorporated by reference herein in its entirety.

Figure 7:
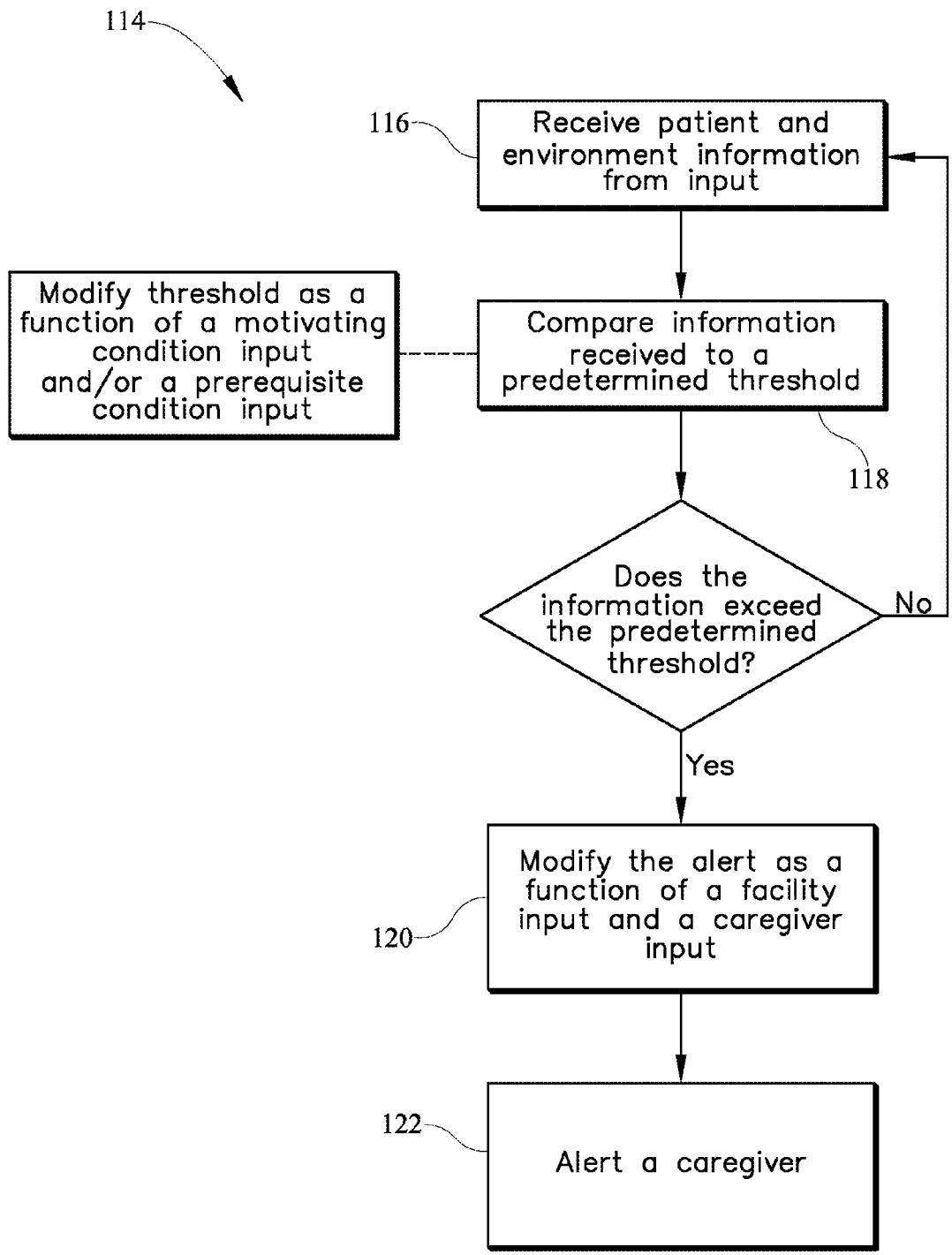
FIG. 7 is a flow chart of a procedure for predicting when a person is going to egress from the person support apparatus according to one contemplated embodiment of the disclosure.

In one contemplated embodiment, the instruction set defines a threshold recognition procedure 114 that causes the processor 100 to send the caregiver an alert via a communication system (not shown) upon determining that a predetermined threshold has been exceeded by the information from the inputs 102 as shown in FIG. 7. Procedure 114 begins with step 116 in which the processor 100 receives patient and environmental information from the input 102. In one example, the information from the input 102 may indicate that the person is awake, the siderail SR is down, and the person is positioned on their side and is using their elbow to prop themselves up. In this instance, a pressure mapping pad can be positioned on the mattress 14 and can identify where the localized pressure increase is with respect to the perimeter of the upper frame 20.

In step 118, the processor 100 compares the information it received in step 116 to a predetermined threshold to determine if/when the person is going to egress from the person support apparatus 12. In one example, if a person has increased the weight supported by their elbow, there may be an increased likelihood that the person will attempt to egress from the person support apparatus 12 in the near future. In some contemplated embodiments, information in the prerequisite condition input and motivating condition input categories can be used to raise or lower the threshold. For example, if the person is awake, the siderail SR is in the storage position, and the person has not toileted in more than 6 hours, the threshold may be lowered because the likelihood that the person will egress from the person support apparatus 14 may be higher.

In step 120 the processor 100 examines information in the facility/unit input and patient/caregiver input categories to determine if the caregiver should be alerted, knowing that an egress event will likely occur. For example, if the information indicates that the caregiver is scheduled to visit the patient within the next few minutes, an alert may not be sent.

Figure 8:
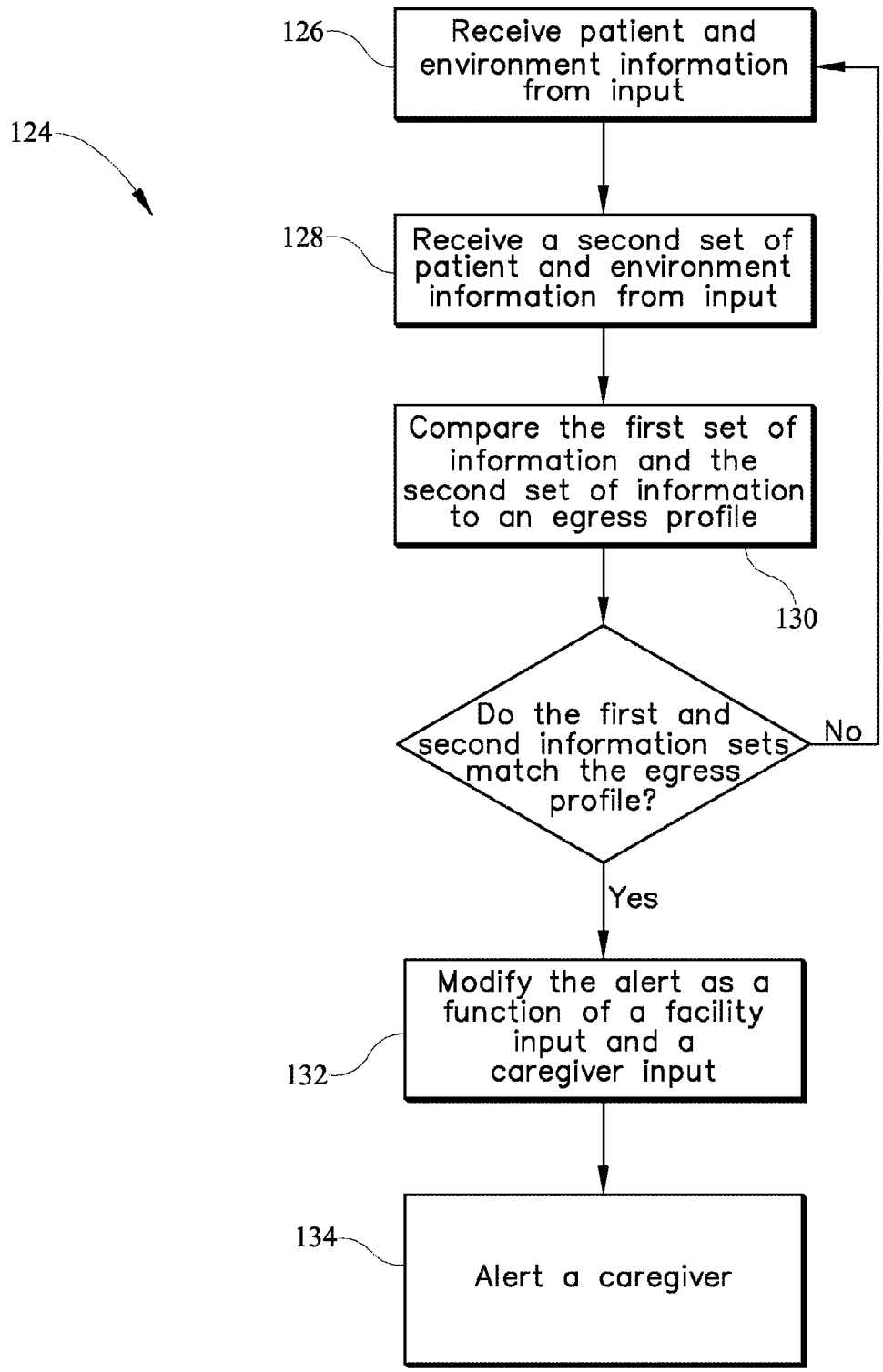
FIG. 8 is a flow chart of a procedure for predicting when a person is going to egress from the person support apparatus according to another contemplated embodiment of the disclosure.

Once it is determined that the person is likely going to exit the person support apparatus 14 in the near future, an alert is sent to the caregiver in step 122. In another contemplated embodiment, the instruction set causes the processor 100 to carry out a sequence recognition procedure 124 that determines if the person's movements over time are indicative of someone who is going to egress from the person support apparatus 12 as shown in FIG. 8. In one example, a sequence of movements that may indicate a person is going to exit the person support apparatus 12 is shown in the table below:

| Input | Analysis |
| --- | --- |
| Sleep sensor or sensing system indicates the patient is sleeping | Exit within the next 10 minutes may be low |
| Sleep sensor or sensing system indicates the patient is waking | Exit within the next 10 minutes may still be low, but may be increased from previous analysis |
| Location/tracking system indicates last toileting 8.2 hours ago | |
| Pressure map indicates leg movement from lateral to bent | Exit within the next 10 minutes may be medium |
| Activity sensor indicates frequent repositioning or fidgeting | |
| Pressure map indicates rotation onto left side | Exit within the next 10 minutes may be high Exit within the next 5 minutes may be medium |
| Pressure map indicates increased weight supported on right elbow | Exit within the next 10 minutes may be high and may be increased from previous analysis Exit within the next 5 minutes may be medium |
| Pressure map indicates increased weight | Exit within the next 10 minutes may be high |

| Input | Analysis |
| --- | --- |
| supported on elbow and increased weight supported on buttocks | and may be increased from previous analysis Exit within the next 5 minutes may be high |

Procedure 124 begins with step 126 where the processor 100 receives a first set of patient and environmental information from the input 102. In one example, the processor 100 receives a first position of the person with respect to the person support apparatus 12.

In step 128 the processor 100 receives a second set of patient and environmental information from the input.

In step 130, the processor 100 compares the second set of information and the first set of information to an egress profile. For example, if a person wakes, turns onto their side, and places their hand on the person support apparatus 12, there may be an increased likelihood that the person will attempt to egress from the person support apparatus 12 in the near future. In other examples, an increased likelihood that the person will attempt to egress from the bed in the near future may be indicated by a pelvis leading and lateral roll for the head and trunk and a lateral lift and push for the far arm, or a legs first see-saw motion for the head and trunk, a reach across the midline and push for the far arm, a multi-push for the near arm, and a synchronous movement of the legs. See *Movement patterns used by the elderly when getting out of bed* by Mount et al. Thomas Jefferson University, Department of Physical Therapy Faculty Papers. In some contemplated embodiments, the egress profile can be learned over time by monitoring the person and identifying common characteristics or patterns that precede the person attempting to egress from the person support apparatus 12. In some contemplated embodiments, the egress profile can be derived from data collected in studies that examine common traits associated with egress from a person support apparatus 12. One example of such a pattern may be where the person repeatedly presses against the siderails to lift their body prior to attempting to egress form the person support apparatus 12. In some contemplated embodiments, repeated motions while the person is sleeping may indicate that the person will attempt to egress from the person support apparatus 12.

In step 132 the processor 100 examines information in the facility/unit input and patient/caregiver input categories to determine if the caregiver should be alerted, knowing that an egress event will likely occur. Once it is determined that the person is likely going to exit the person support apparatus 14 in the near future, an alert is sent to the caregiver in step 134.

Figure 9:
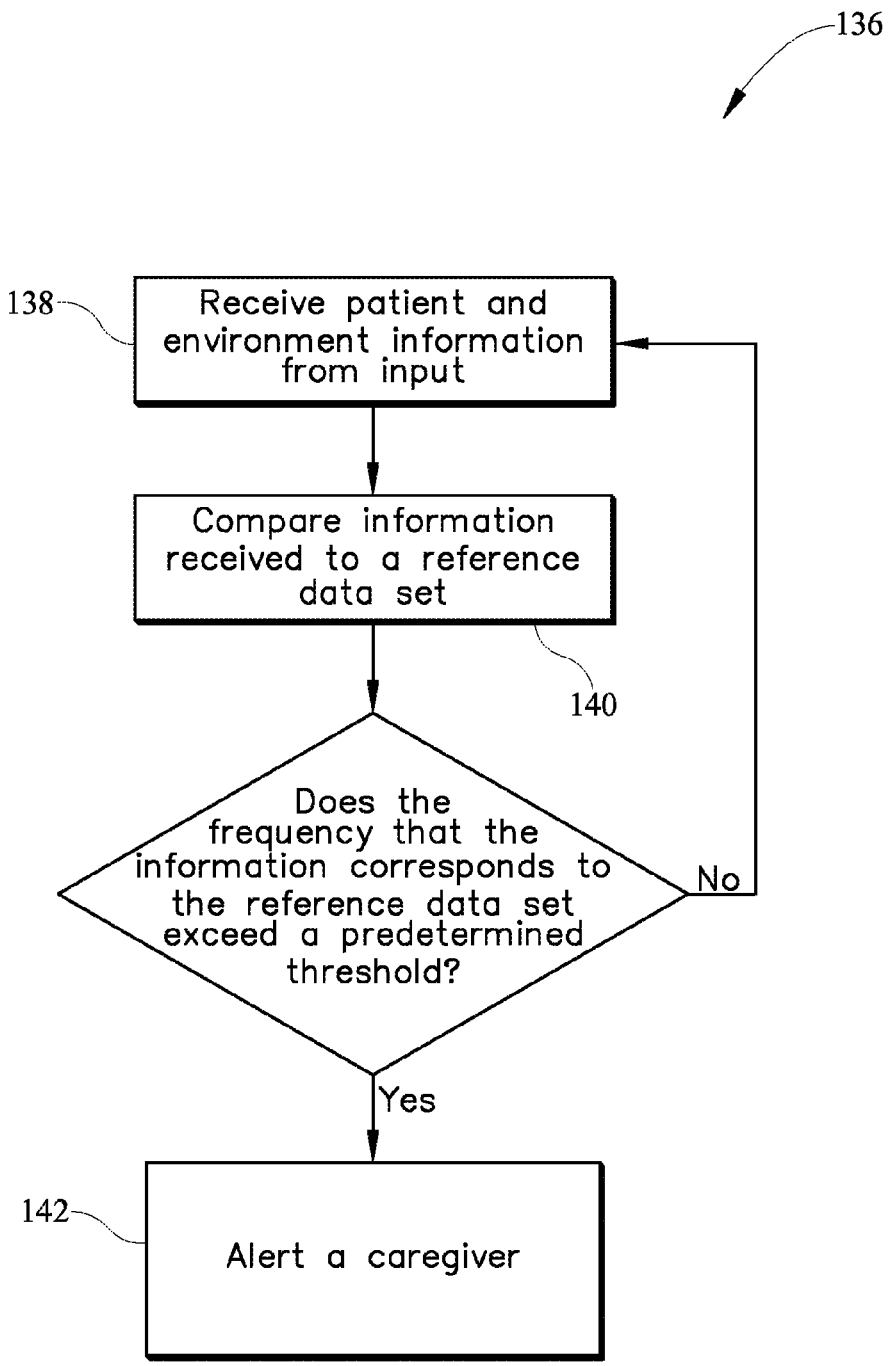
FIG. 9 is a flow chart of a procedure for predicting when a person is going to egress from the person support apparatus according to another contemplated embodiment of the disclosure.

In another contemplated embodiment, the instruction set causes the processor 100 to carry out a data fusion procedure 136 that compares the totality of the inputs with a reference data set to identify patterns correlated with a person preparing to egress as shown in FIG. 9. Procedure 136 begins with step 138 where the processor 100 receives patient and environmental information from the input 102.

In step 140, the processor 100 compares the information corresponding to the person's current pattern of activity with a reference data set to determine the frequency that the current pattern was followed by another person in the reference data set. One example of a way large data sets can be combined and visualized is disclosed in *Visualisation of High-Dimensional Data for Very Large Data Sets* by Wong et al. appearing in Proceedings of the Workshop on Machine Learning for Health Care Applications, 25th International Conference on Machine Learning. Another way the information could be combined and used to predict the likelihood of an egress event is using the Visensia® software sold by OBS Medical.

If the frequency that the pattern follows the reference data set exceeds a predetermined threshold, then the person is likely going to exit the person support apparatus 14 in the near future and an alert is sent to the caregiver in step 142.

Figure 10:
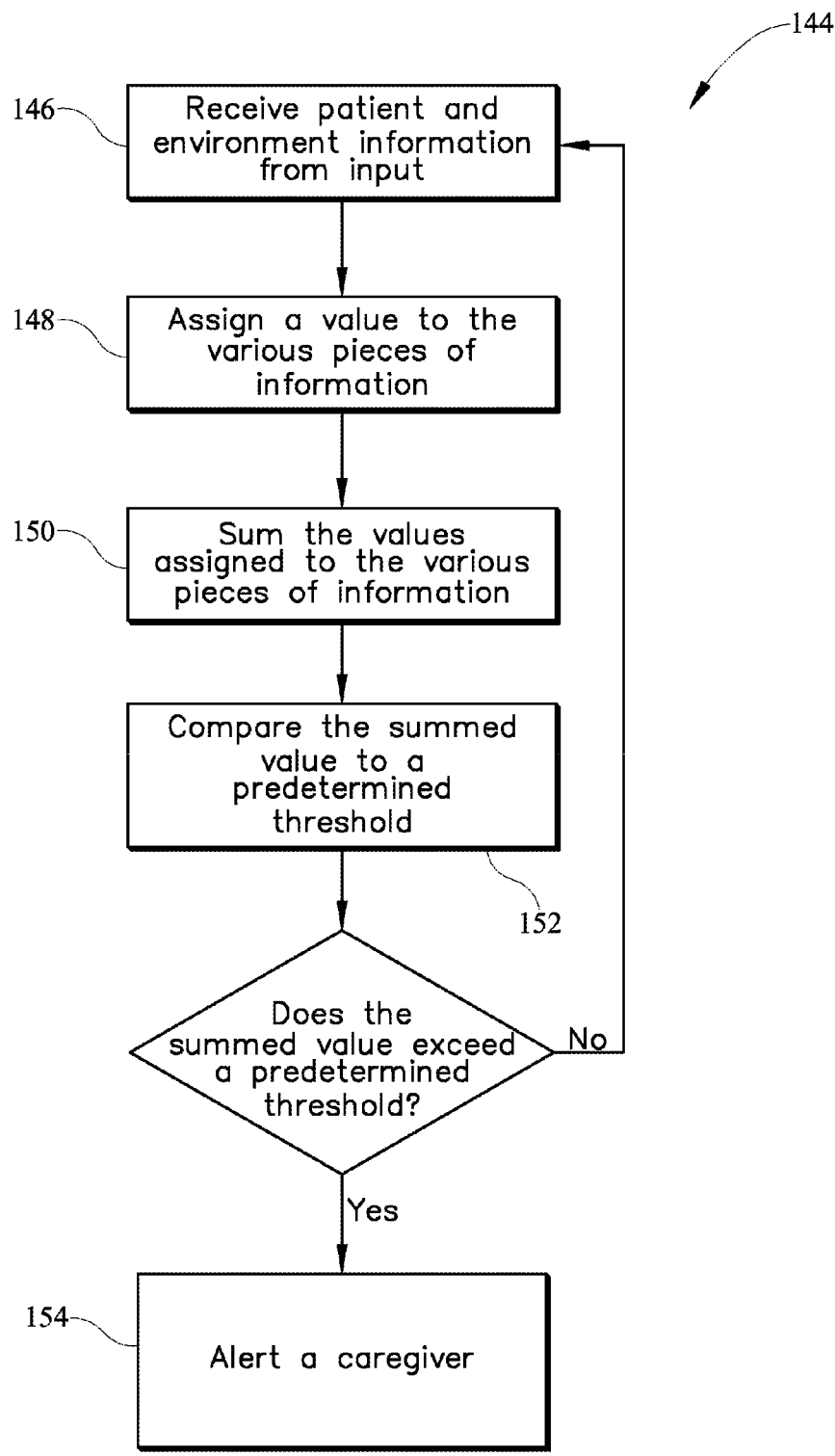
FIG. 10 is a flow chart of a procedure for predicting when a person is going to egress from the person support apparatus according to another contemplated embodiment of the disclosure.

In another contemplated embodiment, the instruction set causes the processor 100 to carry out a multivariate procedure 144 that assigns a value to information and determines if a predetermined threshold value is exceeded as shown in FIG. 10. Procedure 144 begins with step 146 where the processor 100 receives patient and environmental information from the input 102.

In step 148, the processor 100 assigns a value to the various pieces of information based on their relative importance to conditions sensed by the system. In one contemplated embodiment, the value is determined based on statistical analysis of historical data sets showing prior events in similar situations. For example, the following values may be assigned to the information below:

| | |
| --- | --- |
| Walking in the past 10 minutes | 5 points |
| Not catheterized | 2 points |
| No underpad present | 1 point |
| 8 hours since last toileting | 5 points |
| Siderail up | -2 points |
| Activity score 7 | 1 point |

Also based on the historical data, a threshold may be set to identify when a person is likely to egress from the person support apparatus 12. In one example, a person may be very likely to egress from a person support apparatus 14 if they score above 10 points for the information provided above.

In step 150, the processor 100 sums the values assigned to the information.

In step 152, the processor 100 compares the summed value with a predetermined threshold.

If the summed value exceeds the threshold, indicating that the person is likely going to exit the person support apparatus 14 in the near future, an alert is sent to the caregiver in step 154.

Figure 11:
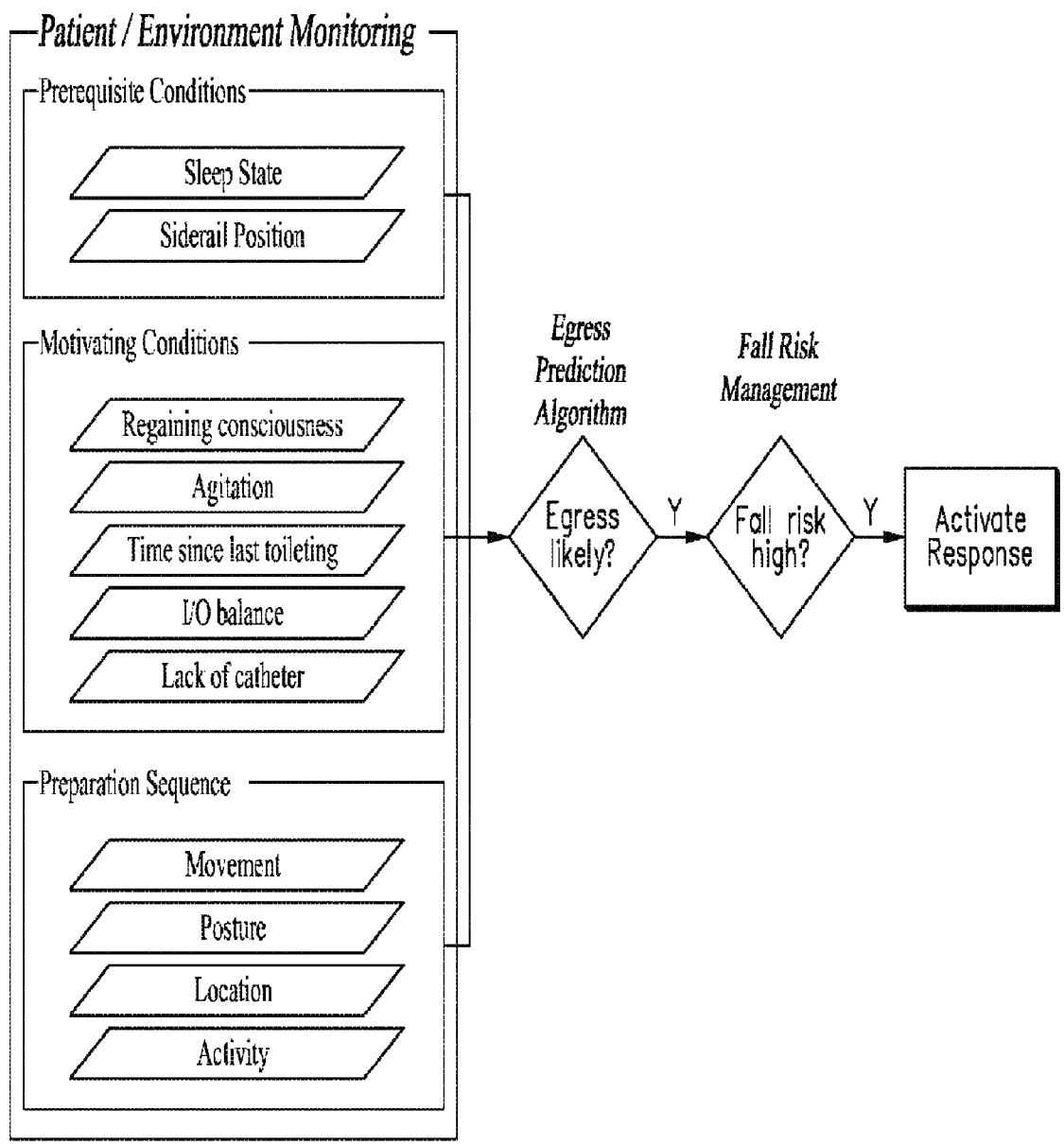
FIG. 11 is a flow chart of a procedure for predicting when a person is going to egress from the person support apparatus according to another contemplated embodiment of the disclosure.

In some contemplated embodiments, multiple procedures or algorithms can act in parallel and can trigger a response as shown in FIG. 11.

In another contemplated embodiment, the control system 16 can provide decision support. For example, the control system 16 can be used to analyze available data to evaluate risk and propose activities to help reduce the risk. In some contemplated embodiments, the system 16 can take into account whether a caregiver is present, what the status of the siderail is, and what the status of the lighting in the room is. In some contemplated embodiments, the system 16 can determine whether the person is a falls risk based on the caregiver assessment, the person's EMR or patient history, and/or the current medical diagnosis and status of the person. The system can also recommend interventions for minimizing the falls risk, such as leaving a walker in the room after physical therapy and/or leaving fluids in the room to reduce dehydration which may exacerbate confusion. In some contemplated embodiments, logged HIPAA compliant data can be uploaded to a central database for analysis. In some contemplated embodiments, algorithms or procedures used by the system 16 may be remotely upgradeable.

Many other embodiments of the present disclosure are also envisioned. For example, a method comprises sensing a first characteristic indicative of an occupant's status on an occupant support structure; sensing a second characteristic indicative of an occupant's status on the occupant support structure; determining if am occupant is preparing to exit the occupant support structure based on the first characteristic and the second characteristic; if an occupant is preparing to exit the occupant support structure, alerting a caregiver. In one contemplated embodiment, determining if an occupant is preparing to exit the occupant support structure by comparing the first characteristic to the second characteristic; if the difference between the first characteristic and the second characteristic is greater than a predetermined threshold, alerting a caregiver that the occupant is preparing to exit the occupant support structure. In another contemplated embodiment, the first and second characteristics are indicative of the occupant's location with respect to the occupant support structure. In another contemplated embodiment, the first and second characteristics are indicative of the occupant's orientation with respect to the occupant support structure. In another contemplated embodiment, the first and second characteristics are indicative of the location of the occupant's center of gravity with respect to the occupant support structure. In another contemplated embodiment, the method further comprises the step of sensing a third characteristic indicative of the occupant's level of consciousness. In another contemplated embodiment, the first and second characteristics are indicative of the occupant's movement with respect to the occupant support structure. In another contemplated embodiment, the first and second characteristics are sensed using at least one fluid pressure sensor coupled to the occupant support structure. In another contemplated embodiment, the first and second characteristics are sensed using a three dimensional sensing device coupled to the occupant support structure. In another contemplated embodiment, the first and second characteristics are sensed using a three dimensional sensing device coupled proximate to the occupant support structure. In another contemplated embodiment, the first and second characteristics are sensed using a video camera coupled to the occupant support structure. In another contemplated embodiment, the first and second characteristics are sensed using a video camera coupled proximate to the occupant support structure. In another contemplated embodiment, the first and second characteristics are sensed using a force sensor coupled to the occupant support structure. In another contemplated embodiment, the first and second characteristics are sensed using a force sensor coupled to a topper positioned on the occupant support structure. In another contemplated embodiment, the method further comprises the steps of: sensing a characteristic of the occupant support structure; and if the characteristic of the occupant support structure is equal to a predetermined value, then alerting a caregiver that the occupant is preparing to exit the occupant support structure. In another contemplated embodiment, the characteristic of the occupant support structure is indicative of the position of the siderail. In another contemplated embodiment, the characteristic of the occupant support structure is indicative of the height of the occupant support structure. In another contemplated embodiment, the characteristic of the occupant support structure is indicative the occupant support structure's configuration. In another contemplated embodiment, the characteristic is indicative of a head end of the occupant support structure being raised. In another contemplated embodiment, the characteristic of the occupant support structure is indicative of the status of a therapy provided by the person occupant support structure. In another contemplated embodiment, the method further comprises the steps of: evaluating a care facility input; and if the characteristic of the care facility is equal to a predetermined value, then alerting a caregiver that the occupant is preparing to exit the occupant support structure. In another contemplated embodiment, the care facility input is indicative of the care facility's protocols. In another contemplated embodiment, the care facility input is indicative of an input from a caregiver. In another contemplated embodiment, the care facility input is indicative of the level of staffing at the care facility. In another contemplated embodiment, the care facility input is indicative of the time of day. In another contemplated embodiment, the care facility input is indicative of an event at the care facility. In another contemplated embodiment, the method further comprises the steps of: determining a motivating condition of the occupant; and if the motivating condition is equal to a predetermined value, then alerting a caregiver that the occupant is preparing to exit the occupant support structure. In another contemplated embodiment, the motivating condition is a noise. In another contemplated embodiment, the motivating condition is an unanswered nurse call. In another contemplated embodiment, the motivating condition is use of a restroom. In another contemplated embodiment, the motivating condition is determined based on information from the occupant's electronic medical record. In another contemplated embodiment, the motivating condition is determined based on information collected by sensors on the occupant support structure. In another contemplated embodiment, the motivating condition is determined as a function of the amount of time that has lapsed since the occupant last exited the occupant support structure. In another contemplated embodiment, the motivating condition is determined as a function of the occupant's medical condition. In another contemplated embodiment, the motivating condition is determined as a function of the type of medication the occupant is taking.

In another example, a system comprises an occupant support structure, a sensor, and a control system. The occupant support structure is configured to support an occupant thereon. The sensor is coupled to the occupant support structure and configured to sense a characteristic of the occupant supported on the occupant support structure. The control system is configured to determine when the occupant is preparing to exit the occupant support structure as a function of the characteristic sensed by the sensor. In one contemplated embodiment, the sensor senses the occupant's position on the occupant support structure. In another contemplated embodiment, the sensor is a load cell. In another contemplated embodiment, the sensor is a force sensor. In another contemplated embodiment, the sensor is a fluid pressure sensor. In another contemplated embodiment, the sensor is a temperature sensor. In another contemplated embodiment, the occupant support structure includes a mattress and a topper positioned on the mattress. In another contemplated embodiment, the topper is a pressure mapping mat. In another contemplated embodiment, the control system determines that an occupant is preparing to exit the occupant support structure when the difference between a current occupant pressure map profile and a previous occupant pressure map profile exceeds a predetermined threshold. In another contemplated embodiment, the occupant support structure includes a lower frame, at least one support coupled to the lower frame, and an upper frame movably supported above the lower frame by the support.

In another example, a method comprises receiving information corresponding to at least one of the position, orientation, and activity level of a person supported on a person support apparatus, determining if the person will likely attempt to egress from the person support structure in the near future based on the information; if the person will likely attempt to egress from the person support structure in the near future, alerting a caregiver. In one contemplated embodiment, determining if the person will likely attempt to egress from the person support structure in the near future by comparing the characteristic to a predetermined threshold; if the characteristic exceeds the predetermined threshold, alerting a caregiver that the person will likely attempt to egress from the person support structure in the near future. In another contemplated embodiment, the threshold is adjusted based on at least one of a prerequisite condition, a caregiver input, a facility input, and a motivating condition. In one contemplated embodiment, the prerequisite condition includes at least one of a status of a siderail and the person's sleep state. In one contemplated embodiment, the motivating condition includes at least one of the time since the person last toileted, the amount of body movement, whether the person can walk, the I/O balance being greater than about 400 ml, the lack of catheterization, and the lack of an incontinence pad. In one contemplated embodiment, the facility inputs include at least one of the level of risk tolerance, care facility protocols, the staffing level of the facility, the time of day, the schedule of rounds for the caregivers, the patient population, the patient case mix, the culture varying patterns of the facility, and the need for detail. In one contemplated embodiment, the caregiver inputs include at least adjustment of the alarms, a personal preference for alarms, and the agitation level of the patient. In one contemplated embodiment, information is received from at least one of an optical camera, an infrared camera, a thermal camera, a Doppler sensing system, an accelerometer, a pressure mapping system, a motion detector, a patient position monitoring system, a center of gravity detecting system, a weight scale system, a caregiver via an input device, an electronic medical record, a patient record, and a pharmacy record.

In another example, a method comprises receiving at least one characteristic of at least one of a person support structure, a person supported on the person support structure, and a facility where the person and the person support structure are located; assigning a value to each of the at least one characteristic; summing the values for the at one characteristic; comparing the summed values to a predetermined threshold; if the summed values exceed the predetermined threshold, alerting a caregiver that the person will likely attempt to egress from the person support structure in the near future.

In another example, a method of predicting an egress condition comprises the steps of: receiving a first input signal indicative of a motivating condition that would cause a person to egress from a person support structure; determining when an egress condition will likely occur based on the first input and generating an alert if an egress condition will occur. In one contemplated embodiment, determining when an egress condition will occur by comparing the first input to a predetermined threshold; and generating an alert if the first input exceeds the predetermined threshold. In another contemplated embodiment, the motivating condition includes time since the person last toileted. In another contemplated embodiment, the time is greater than 6 hours. In another contemplated embodiment, the motivating condition includes absence of an incontinence pad. In another contemplated embodiment, the motivating condition includes I/O balance of greater than 400 mL. In another contemplated embodiment, the motivating condition includes absence of catheterization. In another contemplated embodiment, the motivating condition includes movement of a person with respect to the person support structure increasing over a predetermined period of time.

In another example, a method of predicting an egress condition for a person supported on a person support structure comprises the steps of: receiving an input signal indicative of movement of a person with respect to the person support structure; comparing the input signal to a predetermined egress profile; generating an alert if the input signal is about equal to a portion of the predetermined egress profile. In another contemplated embodiment, the input signal includes information sensed by a pressure map. In another contemplated embodiment, the input signal includes information sensed by a load cell. In another contemplated embodiment, the input signal includes information sensed by an image capture device. In another contemplated embodiment, the input signal includes information sensed by a 3D image sensor. In another contemplated embodiment, the input signal includes information sensed by an array of sensors and the person support structure includes a mattress, wherein the array of sensors is coupled to the mattress.

In another example, a method of predicting an egress condition for a person supported on a person support structure comprises the steps of: receiving input signals corresponding to at least two of: an egress motivating condition; an egress prerequisite condition; an egress preparation sequence; determining when an egress condition will likely occur, and generating an alert if an egress condition will likely occur. In one contemplated embodiment, determining when an egress condition will likely occur by comparing the input signals to a predetermined threshold; and generating an alert if at least one of the input signals exceeds the predetermined threshold. In another contemplated embodiment, the egress motivating condition includes time since the person last toileted. In another contemplated embodiment, the time is greater than 6 hours. In another contemplated embodiment, the egress motivating condition includes absence of an incontinence pad. In another contemplated embodiment, the egress motivating condition includes I/O balance of greater than 400 mL. In another contemplated embodiment, the egress motivating condition includes absence of catheterization. In another contemplated embodiment, the egress motivating condition includes movement of a person with respect to the person support structure increasing over a predetermined period of time. In another contemplated embodiment, the egress preparation sequence includes information sensed by a pressure map. In another contemplated embodiment, the egress preparation sequence includes information sensed by a force sensor. In another contemplated embodiment, the egress preparation sequence includes information sensed by an image capture device. In another contemplated embodiment, the egress preparation sequence includes information sensed by a 3D image sensor. In another contemplated embodiment, the egress preparation sequence includes information sensed by an array of sensors and the person support structure includes a mattress, wherein the array of sensors is coupled to the mattress. In another contemplated embodiment, the egress prerequisite condition includes information indicative of a person's level of consciousness. In another contemplated embodiment, the egress prerequisite condition includes information corresponding to a status of the person support structure. In another contemplated embodiment, the status of the person support structure includes the position of a siderail. In another contemplated embodiment, the egress prerequisite condition includes information corresponding to a status of a therapy. In another contemplated embodiment, at least one of the input signals corresponding to at least one of the egress prerequisite condition and the egress motivating condition is provided by an electronic medical record system. In another contemplated embodiment, at least one of the input signals corresponding to at least one of the egress prerequisite condition and the egress motivating condition is provided by a caregiver via a graphical user interface. In another contemplated embodiment, at least one of the input signals corresponding to at least one of the egress prerequisite condition and the egress motivating condition and the egress preparation sequence is provided by sensors coupled to the person support structure. In another contemplated embodiment, the method further comprises the step of receiving an input signal corresponding to a facility input and modifying the predetermined threshold as a function of the facility input. In another contemplated embodiment, the facility input includes information corresponding to a facility protocol. In another contemplated embodiment, the facility input includes information corresponding to facility logistics. In another contemplated embodiment, the facility input includes information corresponding to at least one of the patient population, case-mix, culture, facility patterns, risk tolerance, time of day, staffing levels, caregiver round times, and likelihood an alert will be responded to within a predetermined amount of time. In another contemplated embodiment, the method further comprises the step of receiving an input signal corresponding to a facility input and modifying the alert as a function of the facility input. In another contemplated embodiment, the method further comprises the step of receiving an input signal corresponding to a caregiver input and modifying the alert as a function of the caregiver input. In another contemplated embodiment, the method further comprises the step of receiving an input signal corresponding to a caregiver input and modifying the predetermined threshold as a function of the caregiver input. In another contemplated embodiment, the caregiver input includes a caregiver alarm preference. In another contemplated embodiment, the alert is communicated to a caregiver via a nurse call system. In another contemplated embodiment, the alert is communicated to a caregiver by the person support structure. In another contemplated embodiment, the person support structure includes an upper frame movably supported above a lower frame by a lift mechanism. In another contemplated embodiment, the person support structure includes a mattress including at least one fluid bladder. In another contemplated embodiment, the egress prerequisite condition includes information corresponding to physiological characteristics of a person supported on the person support structure. In another contemplated embodiment, the egress preparation sequence includes information corresponding to the location of a person supported on the person support structure. In another contemplated embodiment, the egress preparation sequence includes information corresponding to the center of gravity of a person supported on the person support structure. In another contemplated embodiment, the egress preparation sequence includes information sensed by a fluid pressure sensor coupled to a fluid bladder of the person support structure. In another contemplated embodiment, the egress prerequisite condition includes information corresponding to the configuration of the person support structure. In another contemplated embodiment, the egress motivating condition includes an unanswered nurse call. In another contemplated embodiment, the egress motivating condition includes the time since a person last egressed from the person support structure. In another contemplated embodiment, the egress motivating condition includes information corresponding to the medical condition of a person. In another contemplated embodiment, the medical condition of a person includes information corresponding to at least one of a medical procedure a person underwent recently and medication a person is currently taking. In another contemplated embodiment, the egress prerequisite condition includes information corresponding to a fall risk analysis for a person.

In another example, a method of predicting an egress condition for a person supported on a person support structure comprises the steps of: receiving a first input signal corresponding to a characteristic of a person; receiving a second input signal corresponding to a characteristic of a facility; determining when an egress condition will likely occur based on the first input signal, generating an alert to indicate that a person is predicted to egress from the person support structure; and modifying the alert as a function of the second input signal. In one contemplated embodiment, determining when an egress condition will likely occur by comparing the first input signal to a predetermined threshold; if the first input signal exceeds the predetermined threshold. In another contemplated embodiment, the predetermined threshold is modifiable as a function of a third input signal corresponding to an egress motivating condition. In another contemplated embodiment, the predetermined threshold is modifiable as a function of a third input signal corresponding to an egress prerequisite condition.

In another example, a method of predicting an egress condition for a person supported on a person support structure comprises the steps of: receiving a first input signal corresponding to a characteristic of a person; receiving a second input signal corresponding to an input from a caregiver; determining when an egress condition will likely occur based on the first input signal, generating an alert to indicate when an egress condition will likely occur; and modifying the alert as a function of the second input signal. In another contemplated embodiment, the method includes the steps of comparing the first input signal to a predetermined threshold; if the first input signal exceeds the predetermined threshold, generating an alert to indicate that a person is predicted to egress from the person support structure.

In another example, a method of predicting an egress condition for a person supported on a person support structure comprises the steps of: receiving a first input signal corresponding to a characteristic of a person; comparing the first input signal to a predetermined egress profile; if the first input signal matches a portion of the egress profile, generating an alert to indicate that a person is predicted to egress from the person support structure. In another contemplated embodiment, the alert is modifiable as a function of a second input signal corresponding to a characteristic of a facility. In another contemplated embodiment, the alert is modifiable as a function of a second input signal corresponding to an input from a caregiver.

In another example, a method of predicting an egress condition for a person supported on a person support structure comprises the steps of: receiving a plurality of input signals corresponding to at least one of: a characteristic of a person supported on the person support structure; a status of the person support structure; a motivating condition; a prerequisite condition; a preparation sequence; comparing the plurality of inputs to a reference data set; if the frequency that the input signals correspond to the reference data set exceeds a predetermined threshold, generating an alert.

In another example, a method of predicting an egress condition for a person supported on a person support structure comprises the steps of: receiving a plurality of input signals corresponding to at least one of: a characteristic of a person supported on the person support structure; a status of the person support structure; a motivating condition; a prerequisite condition; a preparation sequence; assigning a value to each input signal based on a predetermined list of input value; summing the values for the input signals and comparing the summed value to a predetermined threshold; and generating an alert if the summed value exceeds the predetermined threshold.

In another example, a control system for determining when a person will egress from a person support structure comprises a plurality of input devices, a processor, and a memory unit. The processor is configured to receive input signals from the plurality of input devices corresponding to at least two of: an egress motivating condition, an egress prerequisite condition, and an egress preparation sequence. The memory unit includes instructions that cause the processor to compare the input signals to a predetermined threshold and generate an alert in response to the input signals exceeding the predetermined threshold. In another contemplated embodiment, the memory unit includes instructions that cause the processor to determine when an egress condition is likely to occur based on the input signals and generate an alert if the processor determines that an egress condition is likely to occur. In another contemplated embodiment, the processor and memory are coupled to the person support structure. In another contemplated embodiment, at least one of the plurality of input devices includes a sensor coupled to the person support structure. In another contemplated embodiment, the person support structure includes a mattress including at least one fluid bladder. In another contemplated embodiment, the person support structure includes a frame including an upper frame movably supported above a lower frame by a lift mechanism. In another contemplated embodiment, the egress motivating condition includes time since the person last toileted. In another contemplated embodiment, the time is greater than 6 hours. In another contemplated embodiment, the egress motivating condition includes absence of an incontinence pad. In another contemplated embodiment, the egress motivating condition includes I/O balance of greater than 400 mL. In another contemplated embodiment, the egress motivating condition includes absence of catheterization. In another contemplated embodiment, the egress motivating condition includes movement of a person with respect to the person support structure increasing over a predetermined period of time. In another contemplated embodiment, the egress preparation sequence includes information sensed by a pressure map. In another contemplated embodiment, the egress preparation sequence includes information sensed by a force sensor. In another contemplated embodiment, the egress preparation sequence includes information sensed by an image capture device. In another contemplated embodiment, the egress preparation sequence includes information sensed by a 3D image sensor. In another contemplated embodiment, the egress preparation sequence includes information sensed by an array of sensors and the person support structure includes a mattress, wherein the array of sensors is coupled to the mattress. In another contemplated embodiment, the egress prerequisite condition includes information indicative of a person's level of consciousness. In another contemplated embodiment, the egress prerequisite condition includes information corresponding to a status of the person support structure. In another contemplated embodiment, the status of the person support structure includes the position of a siderail. In another contemplated embodiment, the egress prerequisite condition includes information corresponding to a status of a therapy. In another contemplated embodiment, at least one of the input signals corresponding to at least one of the egress prerequisite condition and the egress motivating condition is provided by an electronic medical record system. In another contemplated embodiment, at least one of the input signals corresponding to at least one of the egress prerequisite condition and the egress motivating condition is provided by a caregiver via a graphical user interface. In another contemplated embodiment, at least one of the input signals corresponding to at least one of the egress prerequisite condition and the egress motivating condition and the egress preparation sequence is provided by sensors coupled to the person support structure. In another contemplated embodiment, the input device is configured to receive an input signal corresponding to a facility input and the instructions cause the processor to modify the predetermined threshold as a function of the facility input. In another contemplated embodiment, the facility input includes information corresponding to a facility protocol. In another contemplated embodiment, the facility input includes information corresponding to facility logistics. In another contemplated embodiment, the facility input includes information corresponding to at least one of the patient population, case-mix, culture, facility patterns, risk tolerance, time of day, staffing levels, caregiver round times, and likelihood an alert will be responded to within a predetermined amount of time. In another contemplated embodiment, the input device is configured to receive an input signal corresponding to a facility input and the instructions cause the processor to modify the alert as a function of the facility input. In another contemplated embodiment, the input device is configured to receive an input signal corresponding to a caregiver input and the instructions cause the processor to modify the alert as a function of the caregiver input. In another contemplated embodiment, the input device is configured to receive an input signal corresponding to a caregiver input and the instructions cause the processor to modify the predetermined threshold as a function of the caregiver input. In another contemplated embodiment, the caregiver input includes a caregiver alarm preference. In another contemplated embodiment, the alert is communicated to a caregiver via a nurse call system. In another contemplated embodiment, the alert is communicated to a caregiver by the person support structure. In another contemplated embodiment, the egress prerequisite condition includes information corresponding to physiological characteristics of a person supported on the person support structure. In another contemplated embodiment, the egress preparation sequence includes information corresponding to the location of a person supported on the person support structure. In another contemplated embodiment, the egress preparation sequence includes information corresponding to the center of gravity of a person supported on the person support structure. In another contemplated embodiment, the egress preparation sequence includes information sensed by a fluid pressure sensor coupled to a fluid bladder of the person support structure. In another contemplated embodiment, the egress prerequisite condition includes information corresponding to the configuration of the person support structure. In another contemplated embodiment, the egress motivating condition includes an unanswered nurse call. In another contemplated embodiment, the egress motivating condition includes the time since a person last egressed from the person support structure. In another contemplated embodiment, the egress motivating condition includes information corresponding to the medical condition of a person. In another contemplated embodiment, the medical condition of a person includes information corresponding to at least one of a medical procedure a person underwent recently and medication a person is currently taking. In another contemplated embodiment, the egress prerequisite condition includes information corresponding to a fall risk analysis for a person.

In another example, a control system for determining a person's position on a person support structure comprises an input device and a controller. The input device is configured to sense the location of a person's heart. The controller is configured to determine if the person is at least one of preparing and attempting to egress from the person support structure as a function of the sensed location of the person's heart. In one contemplated embodiment, the controller alerts a caregiver if the person is determined to be at least one of preparing and attempting to egress.

In another example, a control system for determining when a person will egress from a person support structure comprises a plurality of input devices, a processor, and a memory unit. The processor is configured to receive input signals from the plurality of input devices corresponding to at least two of a patient parameter associated with the likelihood of a patient egressing from the person support structure; an equipment parameter associated with the ability of the patient to egress from the person support structure; and a patient movement parameter indicative of patient movement on the person support structure. The memory unit includes instructions that cause the processor to determine if an egress condition is occurring based upon the input signals and to generate an alert if an egress condition is determined.

In another example, a control system for determining when a person will egress from a person support structure comprises a plurality of input devices, a processor, and a memory unit. The processor is configured to receive a first input indicative of an egress motivating condition. The memory unit includes instructions that cause the processor to determine if an egress condition is likely to occur based on the first input, and to monitor for a second input indicative of at least one of an egress prerequisite condition and an egress preparation sequence.

In another example, a control system for determining when a person will egress from a person support structure comprises a plurality of input devices, a processor, and a memory unit. The processor is configured to receive input signals indicative of the person's sleep state and a person support structure status. The memory unit includes instructions that cause the processor to determine if an egress condition is likely to occur based on the input signals, and generating an alert generate an alert if an egress condition is determined to be likely.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless may not be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and various combinations of inventive aspects and principles are possible in light of the various embodiments provided above.

The invention claimed is:

1. A method of predicting an egress condition for a person supported on a person support structure, the method comprising:
    receiving input signals including: (i) at least one of time since last toileting, input/output balance, or lack of catheter; and (ii) patient position;
    determining if the input signals mimic an egress profile;
    generating an alert if the input signals mimic the egress profile unless the alert is modified; and
    receiving at least one additional input signal corresponding to a facility input and modifying the alert as a function of the facility input, wherein the facility input includes information corresponding to at least one of the following: caregiver round times or likelihood an alert will be responded to by a caregiver within a predetermined amount of time.

2. The method of claim 1, wherein the input signals further include information sensed by a pressure map.

3. The method of claim 2, wherein the pressure map comprises a mat positioned on the mattress.

4. The method of claim 1, wherein the input signals further include information sensed by a load cell.

5. The method of claim 4, wherein the load cell is included as part of a bed frame of the patient support structure.

6. The method of claim 1, wherein the input signals further include information sensed by an image capture device.

7. The method of claim 1, wherein the input signals further include information sensed by a 3D image sensor.

8. The method of claim 1, wherein the input signals further include information sensed by an array of sensors and the person support structure includes a mattress, wherein the array of sensors is coupled to the mattress.

9. The method of claim 1, further comprising communicating the alert to a caregiver via a nurse call system.

10. The method of claim 1, wherein the alert is generated if the time since last toileting is greater than 6 hours.

11. The method of claim 1, wherein the alert is generated if the input/output balance is greater than 400 milliliters (mL).

12. The method of claim 1, wherein at least one of the input signals is received from an electronic medical record system.

13. The method of claim 1, wherein at least one of the input signals is provided by a caregiver.

14. The method of claim 1, wherein at least one of the input signals includes information corresponding to a fall risk analysis of the person.

15. The method of claim 1, wherein at least one of the input signals includes information corresponding to a medical procedure the person underwent.

16. The method of claim 1, wherein at least one of the input signals includes information corresponding to the person's medication.

\* \* \* \* \*